United States Patent [19]

Materne

[11] 4,351,837

[45] Sep. 28, 1982

[54] 1,4-DIHYDROPYRIDINE-3,5-DICARBOXY-LATE-4-CARBOXAMIDE COMPOUNDS, COMPOSITIONS CONTAINING SAME AND METHOD OF USING SAME

[75] Inventor: Carsten Materne, Bonn, Fed. Rep. of Germany

[73] Assignee: Bayer Aktiengesellschaft, Leverkusen, Fed. Rep. of Germany

[21] Appl. No.: 266,274

[22] Filed: May 22, 1981

[30] Foreign Application Priority Data

Jun. 12, 1980 [DE] Fed. Rep. of Germany ....... 3022002

[51] Int. Cl.$^3$ ................ C07D 213/56; C07D 401/12; A61K 31/455
[52] U.S. Cl. .................................... 424/266; 546/281; 546/321; 546/322
[58] Field of Search ...................... 546/321, 322, 281; 424/266

[56] References Cited

U.S. PATENT DOCUMENTS 4,220,649  9/1980  Kojima et al. ...................... 424/266

OTHER PUBLICATIONS

Biellman, Tetrahedron, vol. 26, (20), pp. 4799–4808, (1970).

*Primary Examiner*—Alan L. Rotman
*Attorney, Agent, or Firm*—Sprung, Horn, Kramer & Woods

[57] ABSTRACT

The invention relates to 1,4-dihydropyridine-4-carboxylic acid amines of the formula (I) as defined in the specification. Also included in the invention are methods for the preparation of said compounds. The invention further relates to compositions containing said 1,4-dihydropyridines and the use of said compounds and compositions for their circulation influencing effects.

9 Claims, No Drawings

1,4-DIHYDROPYRIDINE-3,5-DICARBOXYLATE-4-CARBOXAMIDE COMPOUNDS, COMPOSITIONS CONTAINING SAME AND METHOD OF USING SAME

The present invention relates to certain new 1,4-dihydropyridine-4-carboxylic acid amide compounds, to a process for their production, and to their use as medicaments for influencing the circulation.

It is already known that 1,4-dihydropyridine derivatives have circulation-influencing properties. Thus for example, 2,6-dimethyl-4-(2'-nitrophenyl)-1,4-dihydropyridine-3,5-dicarboxylic acid dimethyl ester, a compound known under the Trade Mark "Nifedipin" (see German Patent Specification No. 1,607,827) is known as a compound which has a coronary vasodilating action.

According to the present invention there are provided compounds which are 1,4-dihydropyridines of the general formula $$\text{(I)}$$

or a salt thereof, in which $R^1$ denotes a straight-chain or branched hydrocarbyl radical with 1 to 4 carbon atoms and $R^2$ denotes a branched or straight-chain alkyl radical with 1 to 4 carbon atoms or a $-(CH_2)_m-\underset{R^4}{\underset{|}{N}}\phantom{xx}$, $\phantom{x}-(CH_2)_n-\underset{}{\bigcirc}-R^3$, $-(CH_2)_n-X-(CH_2)_m N\underset{R^6}{\overset{R^5}{\diagdown}}$, or $-NH-\overset{O}{\overset{\|}{C}}-CH_2-N\underset{O}{\diagup}$ radical,
in which
n is 0, 1 or 2,
$R^3$ denotes one or two radicals selected from methyl, hydroxyl and methoxy,
m is 1 or 2,
$R^4$ denotes an alkyl group with 1 to 4 carbon atoms,
$R^5$ and $R^6$ each independently denote an alkyl group with 1 to 4 carbon atoms and
X denotes a $-CH_2-$ group or a hetero-atom, such as O or S.

1,4-Dihydropyridine-4-carboxylic acid amides have not previously been described.

The compounds of the present invention have circulation-influencing properties, and in particular dilate the coronary vessels and lower the blood pressure.

According to the present invention there is further provided a process for the production of compounds of the invention in which a 1,4-dihydropyridine of the general formula $$\text{(II)}$$

in which $R^1$ has the abovementioned meaning, is reacted with an amine of the formula $$H_2N-R^2 \qquad \text{(III)}$$

in which $R^2$ has the abovementioned meaning, in water and/or an inert organic solvent.

Suitable organic solvents are alcohols (particularly alkanols having 1 to 4 carbon atoms, such as methanol, ethanol, isopropanol, etc.), dioxane, ethyl acetate, acetone, methyl ethyl ketone, chloroform and mixtures thereof with each other and with water.

The reaction temperature can be varied within a wide range and is preferably a temperature between 0° C. and 100° C. Most preferably, the reaction is carried out at room temperature.

Compounds of the formula (II) which are used as starting compounds for the process according to the present invention are known compounds or can be prepared in accordance with known processes.

Examples of amines of the formula (III) which are also employed as starting compounds are: 3,4-dimethoxyphenylethylamine, 3,4-dihydroxyphenylethylamine, 3,4-dimethoxybenzylamine, propylamine, isopropylamine, sec.-butylamine, benzylamine, 3,4-dimethoxybenzylamine, 1-ethyl-2-aminomethylpyrrolidine, diethylaminoethylmercaptoethylamine, dimethylaminoethoxyethylamine and pyrrolidin-2-on-1-yl-acetic acid hydrazide.

As stated above, the invention also relates to the use in medicine as circulation-influencing agents of the compounds of the invention.

The present invention provides pharmaceutical compositions containing as active ingredient a compound of the invention in admixture with an inept pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary inert pharmaceutical carriers, e.g. diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene-glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystaline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention.

Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally), subcutaneously and intravenously), rectally or locally.

Administration according to the invention is preferably peroral or intraveneous. In general it has proved advantageous in the case of intravenous administration, to administer about 0.01 to 10 mg/kg, preferably 0.1 to 5 mg/kg bodyweight per day, and, in the case of peroral administration to administer about 0.05 to 20 mg/kg, preferably 0.5 to 50 mg/kg bodyweight per day to achieve effective results.

The following Examples illustrate processes for the production of compounds according to the present invention.

EXAMPLE 1

2,6-Dimethyl-1,4-dihydropyridine-3,4,5-tricarboxylic acid 3,5-diethyl ester 4-(3',4(-dimethoxybenzyl)-amide)

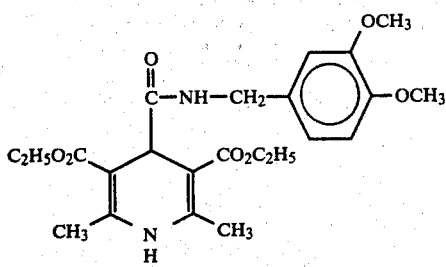

15.7 g. of 3,4-dimethoxybenzylamine were added, at room temperature, to 34.5 g of the mixed anhydride of 2,6-dimethyl-1,4-dihydropyridine-3,4,5-tricarboxylic acid 3,5-diethyl ester and ethyl carbonate, in 50 cm$^3$ of acetone. The mixture was stirred for 2 hours and was then concentrated, and the residue was recrystallised from ethanol.

Yield: 31.2 g (70%).

Melting point: 186° to 190° C.

The following compounds of the present invention were obtained analogously: 2,6-dimethyl-1,4-dihydropyridine-3,4,5-tricarboxylic acid 3,5-diethyl ester 4-isopropylamide, 2,6-dimethyl-1,4-dihydropyridine-3,4,5-tricarboxylic acid 3,5-dimethyl ester 4-butylamide, 2,6-dimethyl-1,4-dihydropyridine-3,4,5-tricarboxylic acid 3,5-diethyl ester 4[2-(3,4-dihydroxyphenyl)-ethyl-]amide, 2,6-dimethyl-1,4-dihydropyridine-3,4,5-tricarboxylic acid 3,5-diethyl ester 4-(3-diethylaminopropyl)-amide, 2,6-dimethyl-1,4-dihydropyridine-3,4,5-tricarboxylic acid 3,5-diethyl ester 4-[2-(2-diethylaminoethyl-mercapto)-ethyl]-amide, 2,6-dimethyl-1,4-dihydropyridine-3,4,5-tricarboxylic acid 3,5-diethyl ester 4-(2,6-dimethyl)-anilide and 2,6-dimethyl-1,4-dihydropyridine-3,4,5-tricarboxylic acid 3,5-diethyl ester 4-[(1-ethylpyrrolidin-2-yl)-methyl]-amide.

EXAMPLE 2

2,6-Dimethyl-1,4-dihydropyridine-3,4,5-tricarboxylic acid 3,5-diethyl ester 4-N'-(pyrrolidin-2-on-1-yl)-acetylhydrazide.

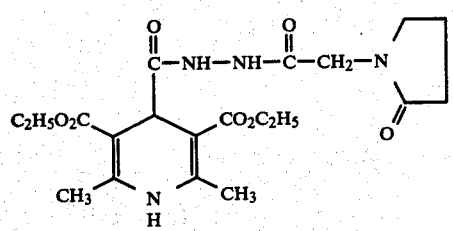

16.3 of pyrrolidin-2-on-1-yl-acetic acid hydrazide in 20 cm$^3$ of CHCl$_3$ were added dropwise to 34.5 g of the mixed anhydride of 2,6-dimethyl-1,4-dihydropyridine 3,4,5-tricarboxylic acid 3,5-diethyl ester and ethyl carbonate, in 100 cm$^3$ of chloroform, at room temperature. The mixture was stirred for 1 to 2 hours and the product was filtered off and recrystallised from methanol/water.

Yield: 31.8 g (73%).

Melting point: 246° to 247° C.

Among the new 1,4-dihydropyridine salts of the invention, those salts that are pharmaceutically acceptable (especially pharmaceutically acceptable acid addition salts) are particularly important and are preferred.

The new free 1,4-dihydropyridines of the general formula (I) and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound which is a 1,4-dihydropyridine of the formula

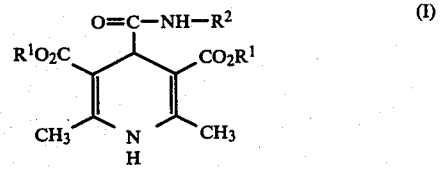

or a pharmaceutically acceptable salt thereof, in which,
R$^1$ denotes a straight-chain or branched hydrocarbyl radical with 1 to 4 carbon atoms and
R$^2$ denotes a

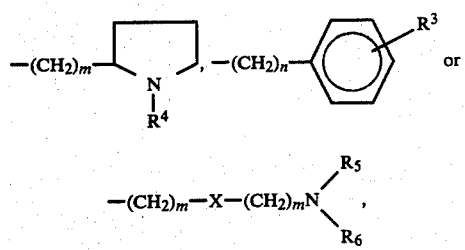

radical,
in which
n is 0, 1 or 2 and
R$^3$ denotes one or two radicals selected from methyl, hydroxyl and methoxy,
m is 1 or 2,
R$^4$ denotes an alkyl group with 1 to 4 carbon atoms,
R$^5$ and R$^6$ each independently denote an alkyl group with 1 to 4 carbon atoms and
X denotes a —CH$_2$— group or a hetero-atom, selected from —O— or —S—.

2. A compound according to claim 1, in which X denotes an oxygen or sulphur atom.

3. A compound according to claim 1 which is 2,6-dimethyl-1,4-dihydropyridine-3,4,5-tricarboxylic acid 3,5-diethyl ester 4-(3', 4'-dimethylbenzyl)-amide.

4. A blood pressure lowering composition comprising as an active ingredient an effective amount of a compound according to claim 1 in admixture with an inert pharmaceutical carrier.

5. A blood pressure lowering composition of claim 4 in the form of a sterile or physiologically isotonic aqueous solution.

6. A blood pressure lowering composition according to claim 4 or 5 comprising from 0.5 to 95% by weight of the said active ingredient.

7. A medicament in dosage unit form comprising an effective amount of a compound according to claim 4.

8. A medicament of claim 7 in the form of tablets, pills, dragees, capsules, ampoules, or suppositories.

9. A method for lowering blood pressure in a warm-blooded animal which comprises administering to said animal a blood pressure lowering effective amount of an active compound according to claim 1.

* * * * *